US00PP21921P3

(12) United States Plant Patent
Bautista

(10) Patent No.: US PP21,921 P3
(45) Date of Patent: May 17, 2011

(54) ***HELICHRYSUM* PLANT NAMED 'HARVEST FIRE'**

(50) Latin Name: *Helichrysum breacteatum*
Varietal Denomination: Harvest Fire

(75) Inventor: Rodolfo Valdoz Bautista, Half Moon Bay, CA (US)

(73) Assignee: Bay City Flower Company, Inc., Half Moon Bay, CA (US)

( * ) Notice: Subject to any disclaimer, the term of this patent is extended or adjusted under 35 U.S.C. 154(b) by 0 days.

(21) Appl. No.: 12/460,164

(22) Filed: Jul. 13, 2009

(65) Prior Publication Data

US 2011/0010814 P1 Jan. 13, 2011

(51) Int. Cl.
*A01H 5/00* (2006.01)

(52) U.S. Cl. ..... Plt./359

(58) Field of Classification Search ..... Plt./359
See application file for complete search history.

*Primary Examiner* — Kent L Bell
(74) *Attorney, Agent, or Firm* — James R. Cypher; Charles R. Cypher

(57) ABSTRACT

A new and distinct cultivar of *Helichrysum* plant named 'Harvest Fire' that originated as a controlled cross. The new variety is distinguished from *Helicyrhsum bracteatum* (Vent.) and all other members of the genera known to the inventor by: the color of it inflorescence and buds, in combination with the ability of its immature inflorescence to develop under indoor light conditions, the resistance of its stems to bending, the resistance of its leaves to scorching, a very compact growth habit, and the ability of its lower buds to develop when the upper inflorescence is cut off without the plant becoming excessively large. The new variety further possesses the following commercially and aesthetically desirable characteristics of resistance to the rood disease Pythium, its puberlent leaves, its ability to grow well in pots, and the ease with which it can be forced to flower for sale in the autumn, and its long-lasting inflorescences.

5 Drawing Sheets

Botanical classification: *Helichrysum* (*bracteatum*×*splendidum*)×*bracteatum.*

Variety denomination: 'Harvest Fire'.

BACKGROUND OF THE INVENTION

This invention relates to a new and distinct cultivar of the Compositae family. The botanical name of the plant is *Helichrysum* (*bracteatum*×*splendidum*)×*bracteatum.*

The new cultivar originated as a seedling from a controlled cross. The controlled hybridization was conducted at a commercial nursery in Half Moon Bay, Calif. The inventor crossed *Helichrysum bracteatum*×*splendidum* 'Raspberry' (U.S. Plant Pat. No. 19,929) with *Helichrysum bracteatum* 'Harvest Nectarine' (U.S. Plant Pat. No. 10,834). *Helichrysum bracteatum*×*splendidum* 'Raspberry' was the seed parent and *Helichrysum bracteatum* 'Harvest Nectarine' was the pollen parent.

The new variety is particularly suitable for commercial plant culture because of its long-lasting inflorescences and attractive colors. The characteristics of the new *Helichyrsum* which in combination distinguish it from other *Helichrysum bracteatum* (Vent.) varieties are: the color of its inflorescences and buds, in combination with the ability of its immature inflorescences to develop under indoor light conditions, the resistance of its leaves to scorching, stems of inflorescences are resistant to rotting and so are more likely to remain upright as the inflorescences ages, a very compact growth habit and so it needs less growth regulators to keep the plant and the desired height for commercial sale, the ability of its lower buds to develop well when the terminal inflorescences are cut off, and even when the terminal inflorescence is cut off and the lower inflorescences develop the plant can still be kept at a desirable height for commercial sale. The new variety further possesses the following commercially and aesthetically desirable characteristics of resistance to the root disease Pythium, its puberlent leaves, its ability to grow well in pots, and the ease with which it can be forced to flower for sale in the autumn, and its long-lasting inflorescences. The inflorescence color of the new variety changes as the involucral bracts age. The bud stage is darkest. The visible lower surface tips of the tightly imbricate involucral bracts are R.H.S. 53 A (red group). As the inflorescence bud begins to open, we see upper side of larger bracts (16 mm long and 8 mm wide—$4^{th}$ of $5^{th}$ whorl of bracts), the upper surface tips are still R.H.S. 53 A (red group), striated with R.H.S. 53 A (red group) in veins remainder of the upper surface of the bract is R.H.S. 7 B (yellow group). As the inflorescence opens further we see upper sides of large, but narrower bracts (17 mm long by 5 mm wide—$8^{th}$ or $9^{th}$ whorl of bracts). The upper surface of these bracts are no longer striated and have an overall color of R.H.S. 23 A (yellow-orange group). As the inflorescence opens further we see upper sides of shorter, narrower and overall smaller bracts (14 mm to 4 mm long by 2 mm wide). The bracts of the innermost whorls have upper and lower bract surfaces which can be as bright as R.H.S. 17 A (yellow-orange group) or as dark as R.H.S. 25 A (orange group). The R.H.S. 25 A (orange group) color in the center of the bracts is the dominant color of the inflorescence. The tips of the outer involucral bracts on the underside of the mature inflorescence retain the color the bracts possessed when the inflorescence began opening.

The following table compares the new variety to varieties known by the inventor to be close to the present invention, according to the new variety's distinguishing characteristics:

Table of Comparison of the New Variety to its Closest Varieties

| | 'Plum' | 'Raspberry' | 'Harvest Nectarine' | New Variety |
|---|---|---|---|---|
| Upper sides mature involucral bracts | Bract tips: R.H.S. 66 D Bract base: R.H.S. 155 C (Tip color dominates in all but innermost bracts) | R.H.S. 58 D | Bract tips: R.H.S. 59 A Bract base: R.H.S. 155 D | R.H.S. 25 A (orange group) is the dominant color |
| Bud color | Bract tips: R.H.S. 187 A Bract Base: R.H.S. 67 B | R.H.S. 187 D (greyed-purple group) | R.H.S. 59 A | The visible lower surfaces have tips that are R.H.S. 53 A (red group) |
| Disease resistance | Resistant to Pythium | Resistant to Pythium | Resistant to Pythium | Resistant to Pythium |
| Hirsute leaves | Puberlent | Puberlent | Hirsute | Puberlent |
| Suitability for pot culture | Good | Good | Good | Good |
| Ease of forcing | Good | Good | Good | Very Good |
| Growth habit | Compact | Compact | Compact | Very compact |
| Inflorescence habit | Long lasting | Long lasting | Long lasting | Long lasting |

The new cultivar 'Harvest Fire' has been successfully asexually reproduced under controlled environmental conditions at a nursery in Half Moon Bay, Calif. under the direction of the inventor over a three successive generations with its distinguishing characteristics remaining stable. Asexual reproduction was first accomplished when vegetative cuttings were used from the initially selected plant.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
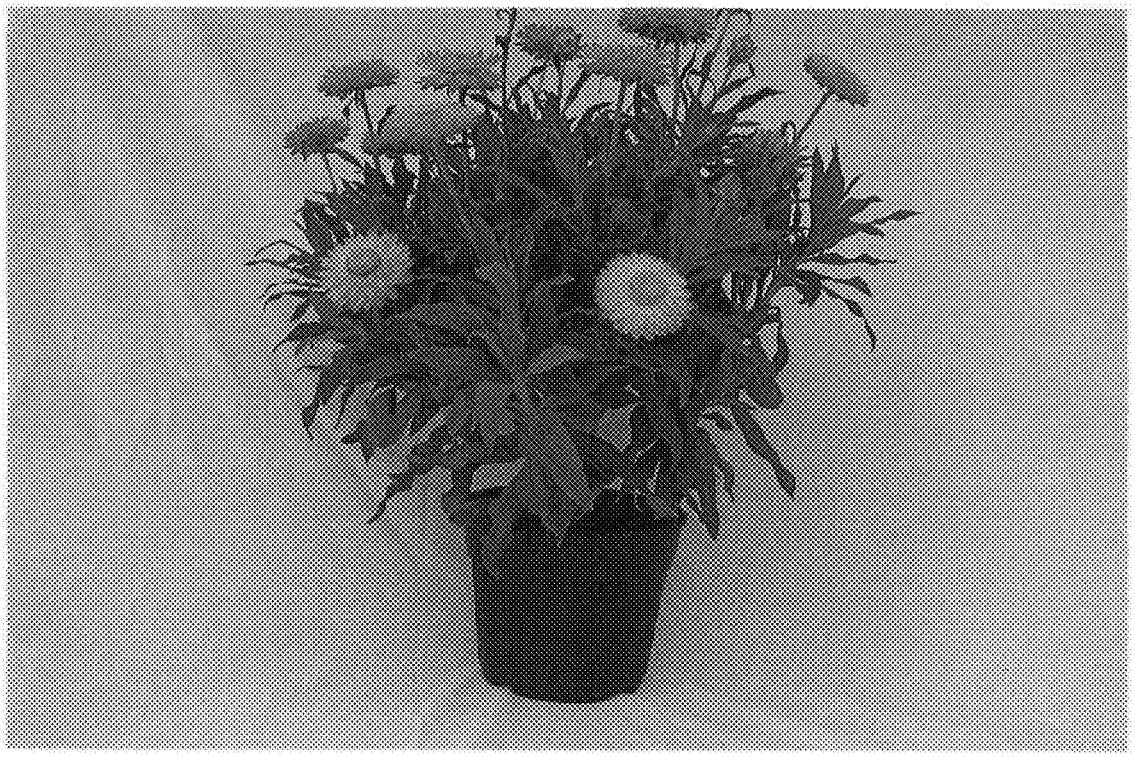
FIG. 1 is a view of the entire plant of the new variety showing its compact growth habit.
Figure 2:
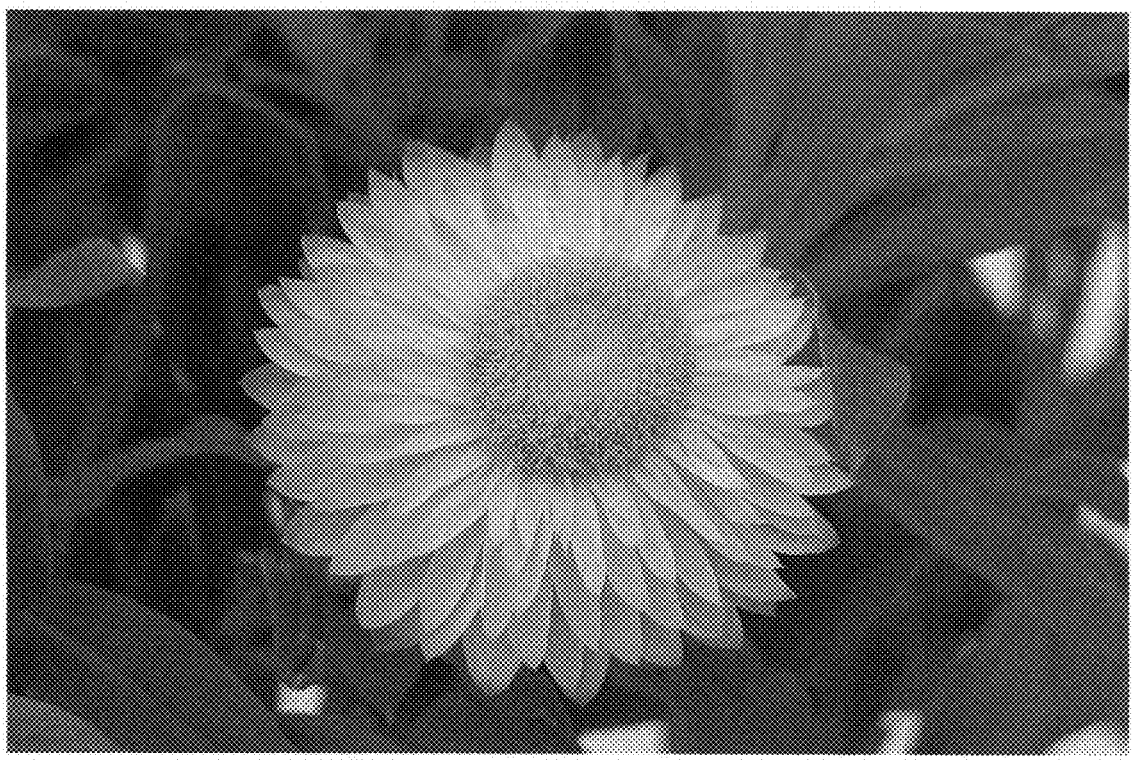
FIG. 2 is a close-up view of a inflorescence of the new variety with all of the involucral bracts reflexed.
Figure 3:
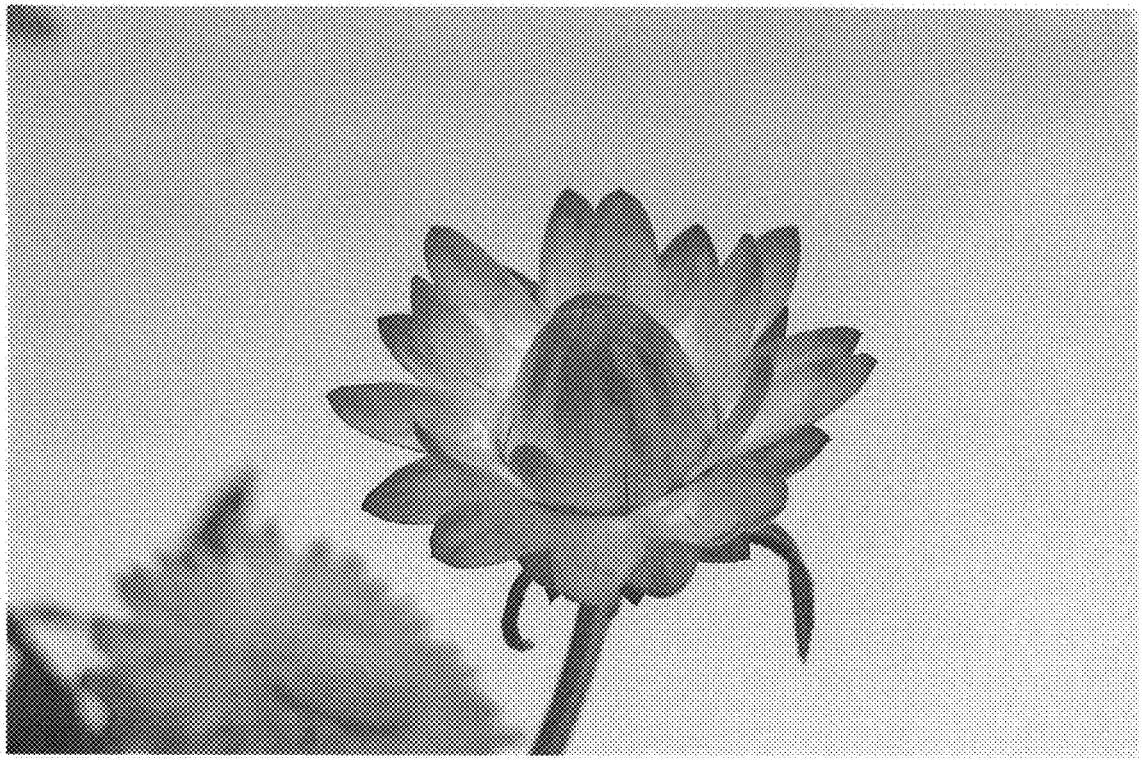
FIG. 3 is a close-up view of a bud that is beginning to open of the new variety.
Figure 4:
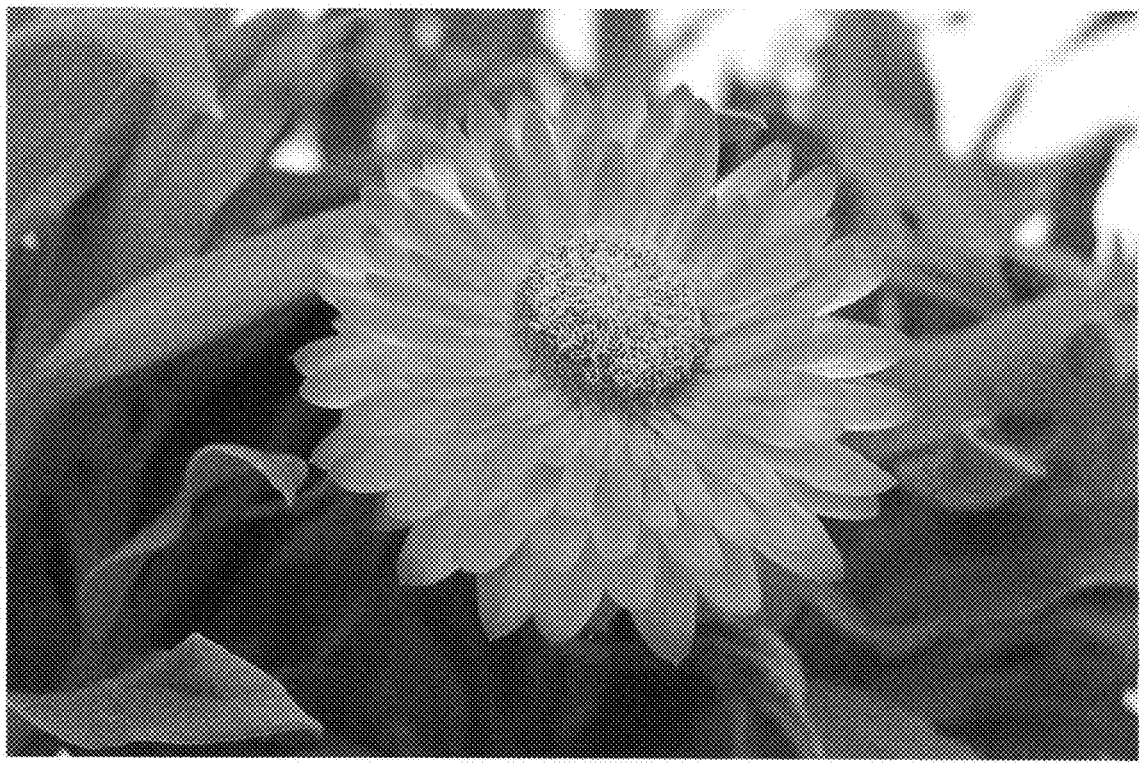
FIG. 4 is a close-up view of a inflorescence of the new variety with all of its involucral bracts reflexed and all of its disc florets opened.
Figure 5:
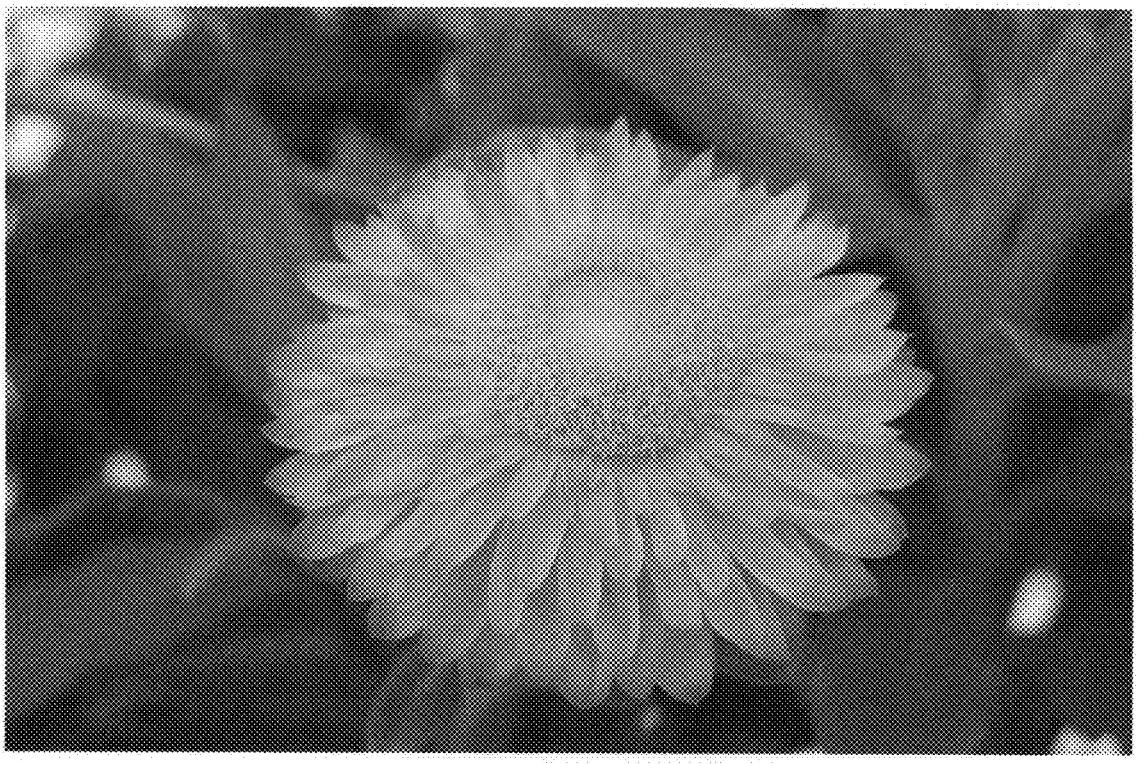
FIG. 5 is a close-up view of a inflorescence of the new variety with all of the involucral bracts reflexed.
Figure 6:
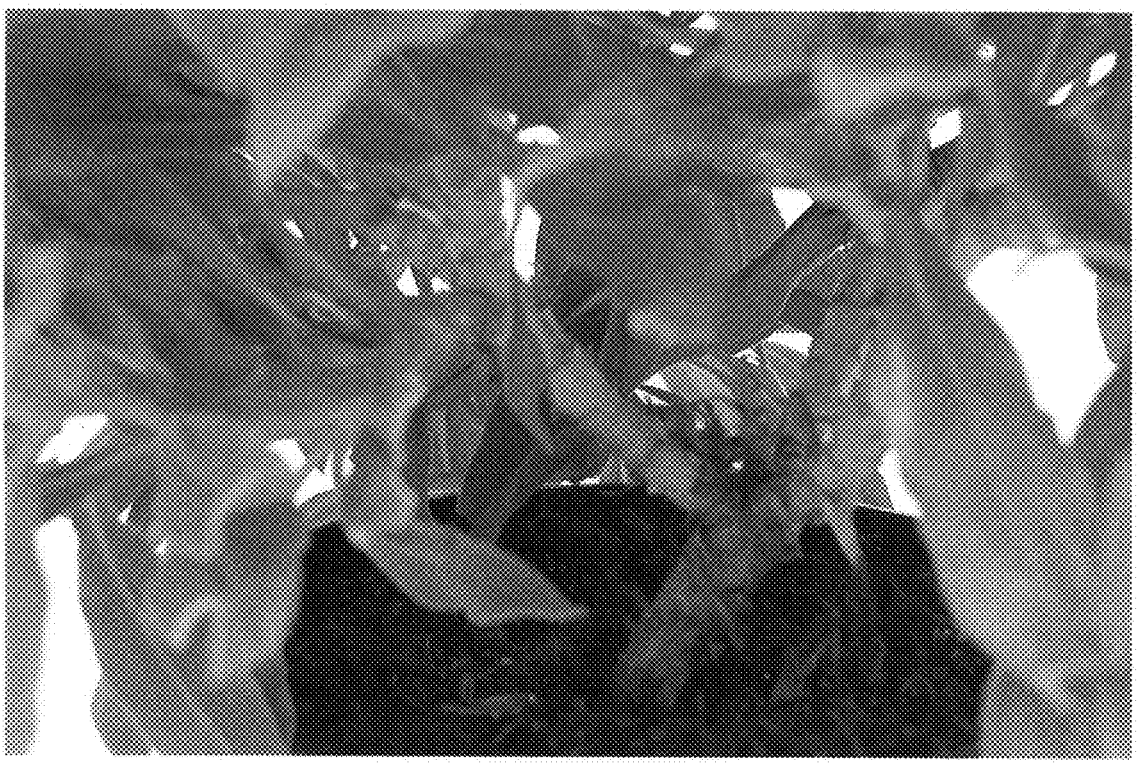
FIG. 6 is a close-up view of the base of the new variety.
Figure 7:
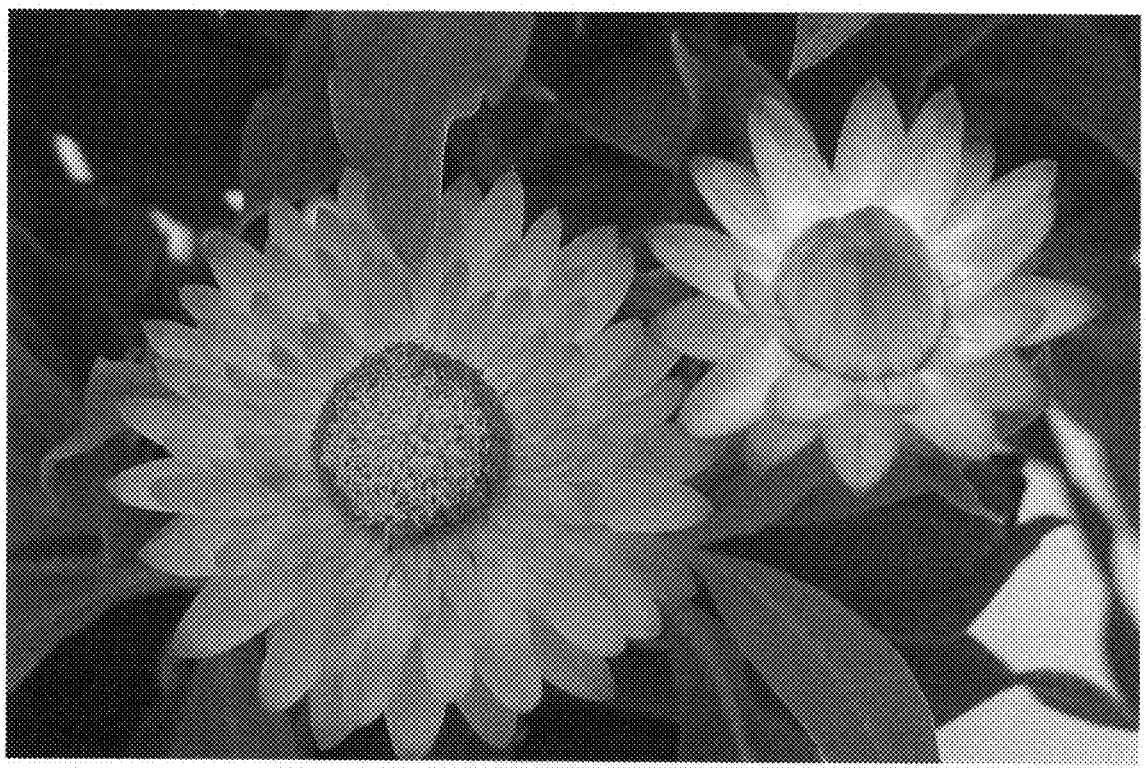
FIG. 7 is a close-up view of two inflorescences of the new variety in different stages of development.
Figure 8:
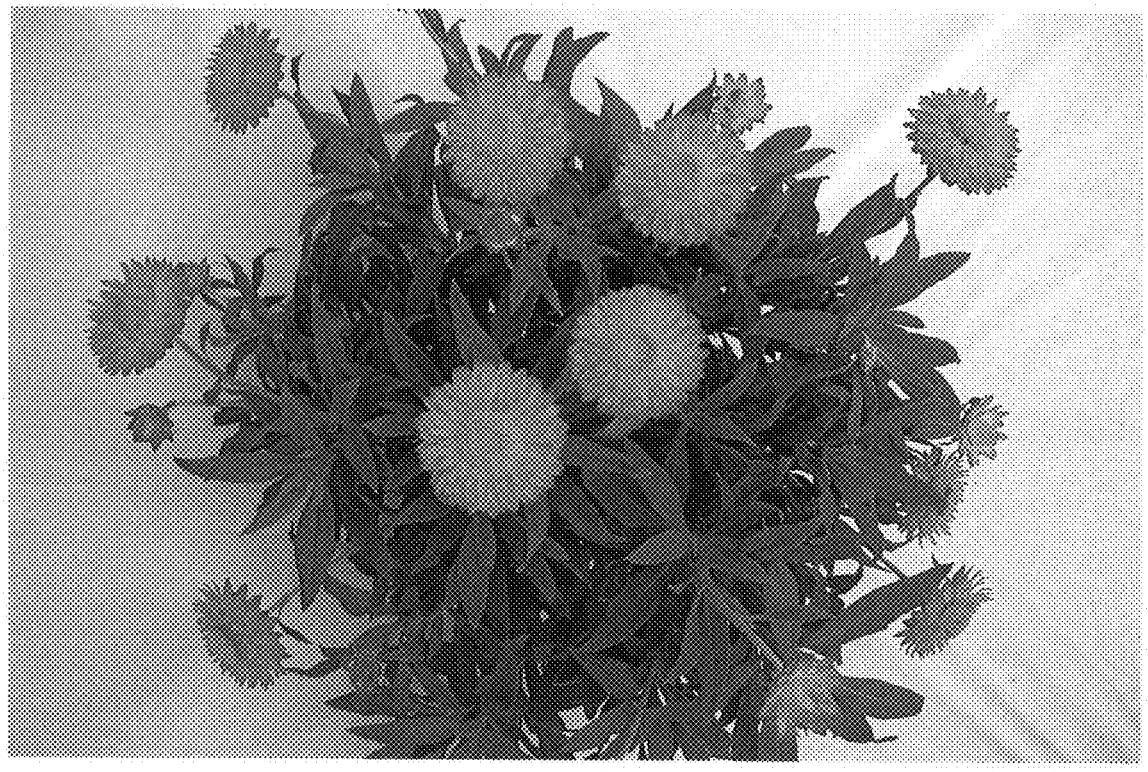
FIG. 8 is a top view of the new variety.
Figure 9:
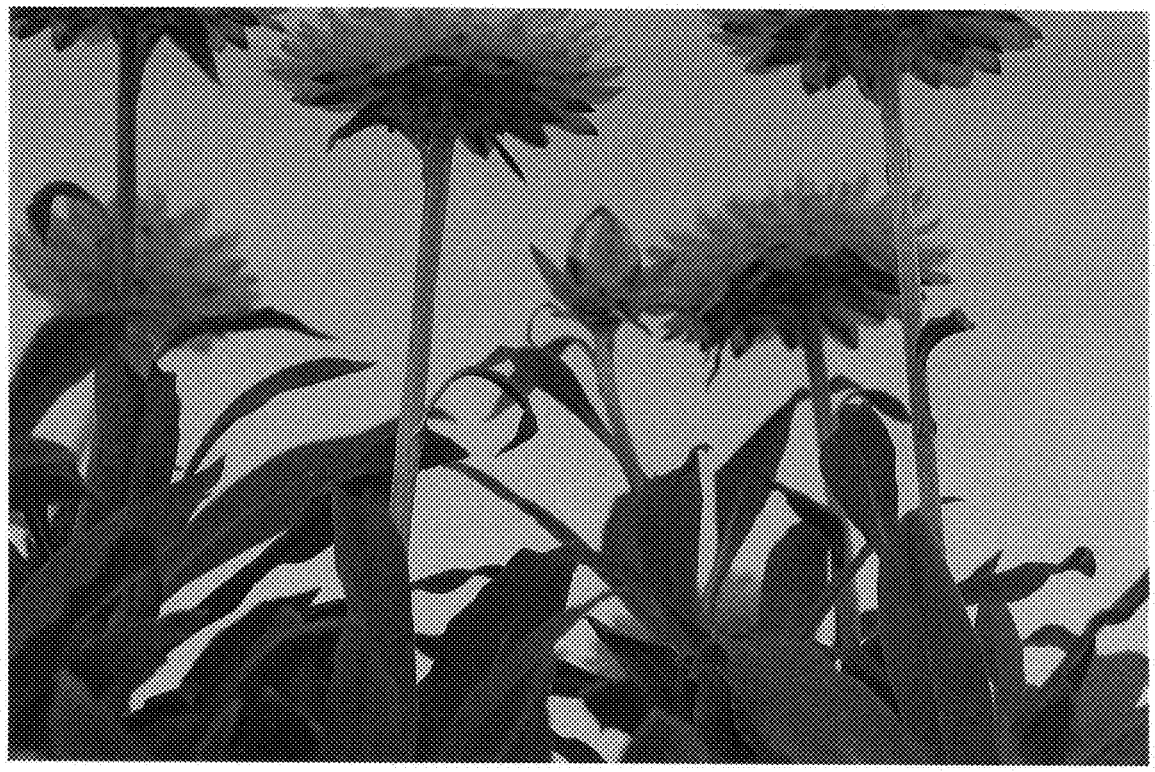
FIG. 9 is a view of the bases of multiple inflorescences of the new variety.
Figure 10:
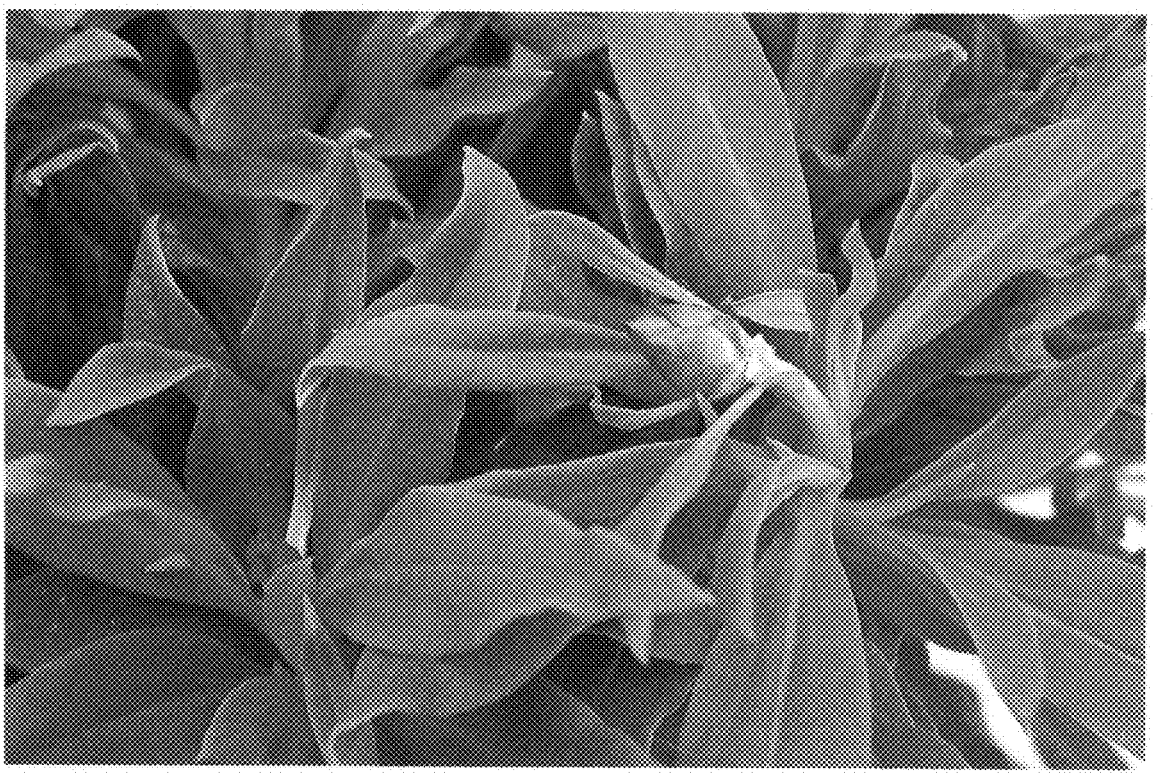
FIG. 10 is a close-up view of two buds of the new variety.

The plants shown in the photographs are ready for commercial sale. The plant started out as cuttings, taken from the stem of a grown plant.

The new variety has not been observed under all possible environmental conditions. The following description is based on observations of optimally fertilized plants with growth regulators applied. The plants were grown in 15.2 cm pots in Half Moon Bay, Calif., during the summer and autumn months. The average temperature during the day was 60 degrees Fahrenheit. The average temperature during the night was 51 degrees Fahrenheit. The phenotype may vary significantly with variations in environment such as temperature, light intensity and day length. Color determinations were made with The Royal Horticultural Society (R.H.S.) Colour Chart.

THE PLANT

Origin: Controlled cross.

Parentage: *Helichrysum bracteatum×splendidum* 'Raspberry' was the seed parent and *Helichrysum bracteatum* 'Harvest Nectarine' was the pollen parent.

Form: Upright, compact biennial shrub. A typical plant with mature inflorescences that is ready for sale is approximately 33 cm high—with inflorescences reaching to 45 cm high—and has a diameter of 45 cm when grown in a 15.2 cm pot with appropriate soil amendments.

Growth: Upright, vigorous growth habit. The plant branches easily. The plant is easily forced to bloom.

Stems: Stems are sericeous giving a glaucous appearance; stems are pubescent below the inflorescence with fine cottony hairs that cover the stem and have a combed, smooth appearance. Stem width just below the inflorescence is 4 mm. Stem width at base of plant is 15 mm. Stems at base of plant are woody—R.H.S. 199 C (gray-brown group). The first portions of the stem that are not woody are 7 mm wide and are R.H.S. 139 D (green group). Stems can be 45 cm high.

Foliage: Abundant.

Shape of leaf.—Linear; narrowly acute; margins are entire but curl somewhat so they appear repand, base is narrowly acute as well.

*Size.*—Leaves are as large as 12 cm long and 2 cm wide.

*Texture.*—Main vein dominates on the underside of the leaf and is sunken on the leaf surface.

*Pubescence.*—Leaf surfaces are puberlent.

*Color.*—Mature leaves have an upper side that is R.H.S. 137 A (green group), and an under side that is R.H.S. 137 C (green group).

*Petiole.*—Nonexistent, semi-amplexicaul attachment of leaves.

Disease resistance: Resistant to the root disease Pythium.

BUDS

Form: Conical and compact, with imbricate involucral bracts.

*Size.*—When fully developed and just beginning to open, buds are 11 mm in diameter and 18 mm in height.

*Texture.*—Smooth and glossy (waxy).

*Rate of opening.*—Slowly, and in layers, closing at night; fully open in 2-3 weeks.

*Involucral bracts.*—The bud stage is darkest of the inflorescence. The tips of the tightly imbricate involucral bracts are R.H.S. 53 A (red group). As the inflorescence bud begins to open, we see upper side of larger bracts (16 mm long and 8 mm wide—$4^{th}$ of $5^{th}$ whorl of bracts) tips still R.H.S. 53 A (red group), striated with R.H.S. 53 A (red group) in veins remainder is R.H.S. 7 B (yellow group).

*Aspect of involucral bracts.*—Thin, dry membranous.

INFLORESCENCE

Form: Inflorescence is discoid and solitary; usually 1 or 2 buds at the next leaf axis below.

*Size of inflorescence.*—Diameter of mature inflorescence is 65 mm, with the disk floret portion being 25 mm.

*Shape.*—Circular; involucral bracts are numerous and imbricate.

*Appearance.*—Showy.

Involucral bracts:

*Form.*—Involucral bracts are imbricate in many rows hundres of involucral bracts on each inflorescence. Involucral bracts are scarious and membranous, but are brightly colored. The involucral bracts are deltoid, enlarged and petal-like with acute tips, entire margins and broad bases.

*Color.*—Inflorescences that are mostly open show the upper sides of large but relatively narrow bracts (17 mm long by 5 mm wide—$8^{th}$ or $9^{th}$ whorl of bracts) that have an overall color of R.H.S. 23 A (yellow-orange group). Inflorescence that are fully opened display upper sides of short and very narrow and overall small bracts (14 mm to 4 mm long by 2 mm wide—innermost whorls) that can be as bright as R.H.S. 17 A (yellow-orange group) or as dark as R.H.S. 25 A (orange group). The R.H.S. 25 A (orange group) color in the center of the bracts is the dominant color of the inflorescence. The tips of the outer involucral bracts on the underside of the mature inflorescence retain the color the bracts possessed when the inflorescence began opening.

Disc florets:

*Form.*—Florets are small, bisexcual and tubular. The corolla of the florets is usually 5-lobed. Corolla is usually 11 mm long and glaucous (waxy) and 3 mm in diameter. The mature florets are R.H.S. 21 A (yellow-orange group). As the florets age past maturity the corolla turns R.H.S. 165 A (greyed-orange group).

*Androecium.*—There are usually 5 stamens borne on the corolla tube. The stamens, including the anthers, are usually united into a tube around the style and become highly reflexed from the point of separation. The stamens protrude from the corolla.

*Gynoecium.*—One pistil per disc floret. The ovary is inferior. The style is often branched. The style protrudes from the corolla. Pistil is R.H.S. 15 A (yellow-orange group).

Persistence: 7 weeks.

Achenes: Inflorescences produce nearly cylindrical or 5-angled achenes that are approximately 3 mm in length and 1 mm in width. The achenes have a pappus of bristles. The bristles can be either simple or plumose at their apex. The achenese are dry and hard The achenes rarely germinate.

I claim:

1. A new and distinct *Helichrysum* plant named 'Harvest Fire' substantially as herein shown and described.

* * * * *